(12) United States Patent
Zhang et al.

(10) Patent No.: US 11,553,713 B2
(45) Date of Patent: Jan. 17, 2023

(54) POLYALCOHOL, CARBOHYDRATE, NUCLEOBASE AND NUCLEOTIDE COMPOSITIONS AND USES THEREOF

(71) Applicant: Chunbo Zhang, Jurupa Valley, CA (US)

(72) Inventors: Chunbo Zhang, San Diego, CA (US); Ligang Qian, San Diego, CA (US); Hongyue Zhang, San Diego, CA (US)

(73) Assignee: Chunbo Zhang, San Diego, CA (US)

( * ) Notice: Subject to any disclaimer, the term of this patent is extended or adjusted under 35 U.S.C. 154(b) by 594 days.

(21) Appl. No.: 15/762,961

(22) PCT Filed: Sep. 21, 2016

(86) PCT No.: PCT/US2016/052940
§ 371 (c)(1),
(2) Date: Mar. 23, 2018

(87) PCT Pub. No.: WO2017/053467
PCT Pub. Date: Mar. 30, 2017

(65) Prior Publication Data
US 2020/0236932 A1 Jul. 30, 2020

Related U.S. Application Data

(60) Provisional application No. 62/233,240, filed on Sep. 25, 2015.

(51) Int. Cl.
| | | |
|---|---|---|
| A01N 31/02 | (2006.01) | |
| A01N 31/06 | (2006.01) | |
| A01N 43/54 | (2006.01) | |
| A01N 43/90 | (2006.01) | |

(52) U.S. Cl.
CPC ............ *A01N 31/02* (2013.01); *A01N 31/06* (2013.01); *A01N 43/54* (2013.01); *A01N 43/90* (2013.01)

(58) Field of Classification Search
None
See application file for complete search history.

(56) References Cited

U.S. PATENT DOCUMENTS

| | | | |
|---|---|---|---|
| 3,856,968 A | 12/1974 | Nikles et al. | |
| 7,820,221 B2 * | 10/2010 | Lang ........................ | A23G 1/54 426/583 |
| 2008/0167374 A1 | 7/2008 | Stickler et al. | |

FOREIGN PATENT DOCUMENTS

| | | |
|---|---|---|
| CN | 101015294 A | 8/2007 |
| CN | 101444485 A | 6/2009 |
| CN | 102090413 A | 6/2011 |
| CN | 102302033 A | 1/2012 |
| CN | 102860303 A | 1/2013 |
| CN | 102885085 A | 1/2013 |
| CN | 104859012 A | 8/2015 |

OTHER PUBLICATIONS

Guenther ("What's it take to produce new pesticides" Jan. 5, 2016 (available online at https://www.grainews.ca/news/whats-it-take-to-produce-new-pesticides/)) (Year: 2016).*
Butt et al (Agricultural Handbook No. 263: Materials Evaluated as Insecticides and Acarides, at Brownsville, Tex., Sep. 1955 to Jun. 1961 (1964)) (Year: 1964).*
International Search Report and Written Opinion for PCT Application No. PCT/US2016/052940, dated Jan. 3, 2017, 9 pages.
Feldwick, M.G. et al., "The Biochemical Toxicology of 1,3-Difluoro-2-propanol, the Major Ingredient of the Psticide Gliftor: The Potential of 4-Methylpyrazole as an Antidote", J Biochem Molecular Toxicology, vol. 12, 1998, pp. 41-52.
Chaubal, R. et al., "Larvicidal Activity of Acacia nilotica Extracts and Isolation of D-Pinitol—A Bioactive Carbohydrate", Chemistry & Biodiversity, vol. 2, 2005, pp. 684-688.
Breuer, M. et al., "Insecticidal activity of the pyrimidine nucleoside analogue (E)-5-(2-bromovinyl)-2'-deoxyuridine (BVDU)", Pest Manag Sci, vol. 61, 2005, pp. 737-741.

* cited by examiner

*Primary Examiner* — Craig D Ricci
(74) *Attorney, Agent, or Firm* — SZDC Law P.C.

(57) ABSTRACT

Disclosed are compositions and methods of pest control. The composition contains one or more active agents such as a polyalcohol, carbohydrate, nucleobase or nucleotide compound or derivative and one or more inactive ingredients which function as attractants or nutrients. The combination of the active agent(s) and the inactive ingredients achieves synergistic effect in pest control.

6 Claims, No Drawings

POLYALCOHOL, CARBOHYDRATE, NUCLEOBASE AND NUCLEOTIDE COMPOSITIONS AND USES THEREOF

CROSS-REFERENCE TO RELATED APPLICATIONS

This patent document is a 35 U.S.C. § 371 National Stage application of International Application No. PCT/US2016/052940 entitled "Polyalcohol, Carbohydrate, Nucleobase and Nucleoside Compositions and Uses Thereof", filed on Sep. 21, 2016, which claims benefit of priority to U.S. Provisional Patent Application No. 62/233,240, entitled "Fluorinated Carbohydrate and Nucleoside Compositions and Uses Thereof," filed on Sep. 25, 2015. The entire contents of the aforementioned patent applications are incorporated by reference as part of the disclosure of this patent document.

TECHNICAL FIELD

This patent document relates to certain chemical compositions and their uses and applications as pesticides.

BACKGROUND

Pesticides are commonly used in agriculture and in our daily life to control various pests and disease carriers such as mosquitoes, ticks, cockroaches, flies, rats, and mice. Most pesticides are chemical compounds or chemical derivatives. Although pesticides have many uses and substantial benefits, pesticides are potentially toxic to humans, animals and other species. Some pesticides have been reported to cause cancer, endocrine disorders, obesity and diabetes, disorders in the nervous system, infertility and sterility, brain damages, birth defects, organ failure, allergies, respiratory disorders (such as asthma) and skin irritation. In the long run, extended or repeated use of pesticides may result in resistance to the pesticides. There is a need for continued development of pesticides which are highly effective in pest control, less toxic to human and environment, and less likely to cause resistance.

SUMMARY

This patent document discloses compositions comprising one or more chemical compounds represented by formulas I to IV shown below and one or more attractants, and uses of the disclosed compositions, including applications that use or are based on the disclosed compositions as pesticides. The chemical compounds disclosed herein include polyalcohol, carbohydrate, nucleobase and nucleoside compounds and derivatives thereof.

In one aspect, this patent document discloses a composition comprising one or more of the active agents represented by formulas I to IV, and one or more attractants or nutrients. The composition can be used for pest control. In some embodiments, the active agent includes a polyalcohol, or a carbohydrate represented by formula I or formula II:

$$R^1-(CR^2OH)n-CR^3F-(CR^4OH)m-R^5 \qquad \text{A) Formula I}$$

wherein:
each of $R^1$ through $R^4$ includes H, I, F, Cl, Br, CHO, $SR^6$, $CONHR^6$, $CON(R^6)_2$, $COOR^6$, an alkyl, an alkoxyl, an aralkyl, or an aryl group having 1 to 9 carbon atoms;
n or m is an integer, preferably from 0-9;
$R^5$ includes H, CHO, $CONHR^6$, $CON(R^6)_2$, or $COOR^6$; and
$R^6$ includes H, an alkyl, an aralkyl, or an aryl group having 1 to 9 carbon atoms;
or $$X-CR^1R^2-[CR^{7n}R^{8n}]_m-CR^3R^4-Y \qquad \text{B) Formula II}$$

wherein:
m is an integer, preferably from 0 to 9;
n is a variable from 1 to m;
each of X and Y includes H, I, F, Cl, Br, CHO, OH, $NH_2$, $NO_2$, $OR^5$, $SR^5$, $CONR^5R^6$, $NHCOR^5$, $COOR^5$, $NR^5OR^6$, $NR^5R^6$, or $PR^5R^6$;
X/Y can be —O—, —S—, —P($R^5$)—, or N($R^5$)—;
each of $R^1$ through $R^4$, and $R^{7n}$ and $R^{8n}$, includes H, I, F, Cl, Br, CHO, OH, $NH_2$, $NO_2$, $OR^5$, $SR^5$, $CONR^5R^6$, $NHCOR^5$, $COOR^5$, $NR^5OR^6$, $NR^5R^6$, $PR^5R^6$, or from alkyl, alkoxyl, aralkyl, aryl or cycloalkyl groups having 1 to 9 carbon atoms;
each of R5 and R6 includes H, alkyl, alkoxyl, aralkyl, aryl or cycloalkyl groups having 1 to 9 carbon atoms; and
$R^1/R^2$, $R^1/R^3$, $R^3/R^4$, $R^1/R^{7n}$, or $R^{7n}/R^{8n}$ can be —O—, —S—, —P($R^5$)—, N($R^5$)—, or a cycloalkyl group having 1 to 9 carbon atoms.

In other embodiments, the active agent includes a nucleobase or nucleoside derivative represented by either formula III or formula IV:

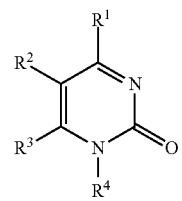

Formula III

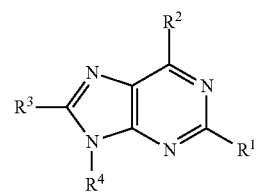

Formula IV wherein:
each of $R^1$, $R^2$ and $R^3$ includes H, F, $OR^5$, I, Cl, Br, CHO, $SR^5$, $CONHR^5$, $CON(R^5)_2$, $COOR^5$, an alkyl, an alkoxyl, an aralkyl or an aryl group having 1 to 9 carbon atoms;
$R^4$ includes fluorinated or non-fluorinated carbohydrates, or polyhydroxy compounds having 1 to 9 carbon atoms; and
$R^5$ includes H, an alkyl, an aralkyl, or an aryl group having 1 to 9 carbon atoms.

In some embodiments, a composition disclosed herein includes one or more active agents and one or more attractants. An active agent disclosed herein is selected from the group consisting of compounds represented by formula I, formula II, formula III, and formula IV:

$$R^1-(CR^2OH)n-CR^3F-(CR^4OH)m-R^5 \qquad \text{A) Formula I}$$

wherein:
each of $R^1$ through $R^4$ is selected from the group consisting of H, I, F, Cl, Br, CHO, $SR^6$, $CONHR^6$, $CON(R^6)_2$, $COOR^6$, an alkyl, an alkoxyl, an aralkyl, and an aryl group having 1 to 9 carbon atoms;
n or m is an integer, preferably from 0-9;

$R^5$ is selected from the group consisting of H, CHO, CONHR$^6$, CON(R$^6$)$_2$, and COOR$^6$; and $R^6$ is selected from the group consisting of H, an alkyl, an aralkyl, or an aryl group having 1 to 9 carbon atoms;

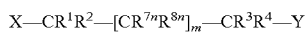    B) Formula II wherein:

m is an integer, preferably from 0 to 9;

n is a variable from 1 to m;

each of X and Y is selected from the group consisting of H, I, F, Cl, Br, CHO, OH, NH$_2$, NO$_2$, OR$^5$, SR$^5$, CONR$^5$R$^6$, NHCOR$^5$, COOR$^5$, NR$^5$OR$^6$, NR$^5$R$^6$, and PR$^5$R$^6$;

X/Y is selected from the group consisting of —O—, —S—, —P(R$^5$)—, and N(R$^5$)—;

each of R$^1$ through R$^4$, and R$^{7n}$ and R$^8$, is selected from the group consisting of H, I, F, Cl, Br, CHO, OH, NH$_2$, NO$_2$, OR$^5$, SR$^5$, CONR$^5$R$^6$, NHCOR$^5$, COOR$^5$, NR$^5$OR$^6$, NR$^5$R$^6$, PR$^5$R$^6$, and alkyl, alkoxyl, aralkyl, aryl or cycloalkyl groups having 1 to 9 carbon atoms;

each of R5 and R6 is selected from the group consisting of H, alkyl, alkoxyl, aralkyl, aryl and cycloalkyl groups having 1 to 9 carbon atoms; and R$^1$/R$^2$, R$^1$/R$^3$, R$^3$/R$^4$, R$^1$/R$^{7n}$, or R$^{7n}$/R$^{8n}$ is selected from the group consisting of —O—, —S—, —P(R$^5$)—, N(R$^5$)—, and a cycloalkyl group having 1 to 9 carbon atoms;

C) Formula III:

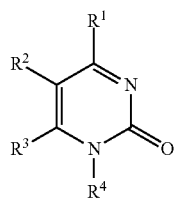

Formula III wherein:

each of R$^1$, R$^2$ and R$^3$ is selected from the group consisting of H, F, OR$^5$, I, Cl, Br, CHO, SR$^5$, CONHR$^5$, CON(R$^5$)$_2$, COOR$^5$, an alkyl, an alkoxyl, an aralkyl and an aryl group having 1 to 9 carbon atoms;

R$^4$ is selected from the group consisting of fluorinated or non-fluorinated carbohydrates, and polyhydroxy compounds having 1 to 9 carbon atoms; and R$^5$ is selected from the group consisting of H, an alkyl, an aralkyl, and an aryl group having 1 to 9 carbon atoms; and D) Formula IV:

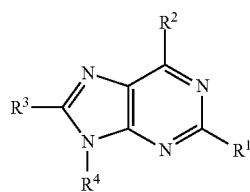

Formula IV wherein:

each of R$^1$, R$^2$ and R$^3$ is selected from the group consisting of H, F, OR$^5$, I, Cl, Br, CHO, SR$^5$, CONHR$^5$, CON(R$^5$)$_2$, COOR$^5$, an alkyl, an alkoxyl, an aralkyl and an aryl group having 1 to 9 carbon atoms;

R$^4$ is selected from the group consisting of fluorinated or non-fluorinated carbohydrates, and polyhydroxy compounds having 1 to 9 carbon atoms; and R$^5$ is selected from the group consisting of H, an alkyl, an aralkyl, and an aryl group having 1 to 9 carbon atoms.

The compositions disclosed herein can include one or more active agents of the same formula or of different formulas.

In some embodiments, the active agent is or includes 3-fluoropropane-1,2-diol, either in R-form or S-form. In other embodiments, the active agent can include fluoropropanediols, allyloxypropanediols, benzyloxypropanediols, bromopropanediols, chloropropanediols, cyclohexanediols, methoxypropanediols, morpholinopropanediols, iodopropanediols, phenoxypropanediols, phenylpropanediols, piperidinopropanediols, trimethylsilylpropanediols, oxanediols, hydroxycyclohexanones, difluoopropanol, dibromopropanol, dichloropropanol, diiodopropanol, 2-(bromomethyl)-2-(hydroxymethyl)-1,3-propanediol, 1,4-butanediol, 1,2,4-butanetriol, 2-butyl-2-ethyl-1,3-propanediol, 2-chloro-3-hydroxy proponic acid, 2-chloropropionic acid, 1,2,3,4-cyclohexanctetrol, 2,2-diethyl-1,3-propanediol, 4-deoxy-4-bromo-D-glucopyranose, 4-deoxy-4-chloro-D-glucopyranose, 4-deoxy-4-fluoro-D-glucopyranose, 2'-deoxy-5-fluorouridine 1,3-dihydroxyacetone, 4-deoxy-4-iodo-D-glucopyranose, 2,2-dimethyl-1,3-propanediol, 2,2-dipropyl-1,3-propanediol, 2-ethyl-2-methyl-1,3-propanediol, 2-fluoroadenine, 3-fluoro-4-hydroxypentan-2-one, gemcitabine, 1,3-hexanediol, 2-hydroxymethyl-cyclopentanol, 3-isopropylamino-1,2-propanediol, 2-methyl-1,3-propanediol, 3-methylamino-1,2-propanediol, or 1,3,4,-trihydroxy-butan-2-one.

In some embodiments, the concentration of the one or more active agents is from 0.001% to 1%, from 0.1% to 25%, from 0.5% to 20%, from 1% to 15%, from 3% to 10%, or from 5% to 8% of the total weight of the composition.

In some embodiments, the attractant includes a food attractant, a sex attractant, an olfactory attractant, or an environmental attractant. The environmental attractant can be a desired pH value, light, sound, vibration, wind, heat, humidity, and gas and can be artificially created by one or more devices. One or more attractants of the same or different types can be included in the composition.

In some embodiments, the composition includes a combination of attractants comprising four or more chemicals that include sucrose, dextrose, sodium citrate, citric acid, sodium monobasic phosphate, or adenine.

In some embodiments, the concentration of the one or more attractants is from 0.001% to 1%, from 1% to 50%, from 5% to 45%, from 10% to 30%, or from 15% to 25% of the total weight of the composition.

In some embodiments, the composition kills at least 10%, at least 20%, at least 30%, at least 40%, at least 50%, at least 60%, at least 70%, at least 80%, at least 90%, or about 100% of the population of the pests upon ingestion of the composition.

In another aspect, this patent document discloses a method of pest control comprising exposing a population of pests to the compositions described above.

In yet another aspect, this patent document discloses a method of preventing a pest-borne, infectious disease comprising exposing a population of pests to the composition described above.

Those and other aspects and their implementations and applications are described in greater detail in the description and the claims.

DETAILED DESCRIPTION

Specific examples for compositions containing active agents represented by formulas I to IV and derivatives are described, including using these compositions as pesticides.

I. Pesticides and Pest Control

According to the U.S. Environmental Protection Agency (EPA), the term "pesticide" means any substance or mixture of substances intended for preventing, destroying, repelling, or mitigating any pest. In the context of this patent document, pests are living organisms that cause damages to plants including household plants, ornamental plants and crops, and to humans or other animals. Exemplary pests include, but are not limited to, insects, rodents, weeds, fungi, plant pathogens, microorganisms such as bacteria and viruses, and prions. Thus, pesticides as used herein include, but are not limited to, herbicides, fungicides, insecticides, nematicides, termiticides, molluscicides, piscicides, avicides, rodenticides, predacides, bactericides, acaricides, pediculicides, algaecides, insect growth regulators, plant growth regulators, insect repellents, and animal repellents. Pests can be household pests or agriculture pests. Common household pests include but are not limited to mosquitoes, flies, bedbugs, fleas, ticks, cockroaches, termites, ants, rodents (e.g., mice and rats), etc.

Pest-borne diseases impose a great risk upon the health of humans and animals and can even cause deaths. For example, mosquito bites spread a number of diseases such as dengue fever, yellow fever, malaria, pogosta disease, Eastern Equine Encephalitis, West Nile virus, and Zika virus. Flies are a major transmitter of diseases (e.g., hepatitis, typhoid, cholera and dysentery) and pathogens (e.g., *Salmonella*, anthrax, tuberculosis, and eggs of parasitic worms). Tick bites spread Lyme disease, Babesiosis, and Ehrlichiosis/Anaplasmosis. Cockroaches can cause allergies and asthma and carry many pathogens such as *E. coli, Salmonella*, and parasitic worms.

Therefore, an effective pest control is very important for preventing and combating these pest-borne infectious diseases. For example, use of insecticides that target adult mosquitoes has resulted in significant progress in fighting against the diseases transmitted by mosquitoes. Although insecticides are presently available on the market, resistance to these insecticides is a serious issue. New classes of insecticides are urgently needed.

II. Polyalcohols, Carbohydrates or their Derivatives as the Active Agents

The active agent can be a chemical compound having a molecular formula I or formula II:

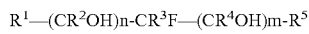
A) Formula I wherein:
each of $R^1$ through $R^4$ includes H, I, F, Cl, Br, CHO, $SR^6$, $CONHR^6$, $CON(R^6)_2$, $COOR^6$, an alkyl, an alkoxyl, an aralkyl, or an aryl group having 1 to 9 carbon atoms;
n or m is independently an integer, preferably from 0-9;
$R^5$ includes H, CHO, $CONHR^6$, $CON(R^6)_2$, or $COOR^6$; and
$R^6$ includes H, an alkyl, an aralkyl, or an aryl group having 1 to 9 carbon atoms; or

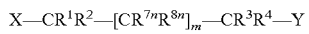
B) Formula II wherein:
m is an integer, preferably from 0 to 9;
n is a variable from 1 to m;

each of X and Y includes H, I, F, Cl, Br, CHO, OH, $NH_2$, $NO_2$, $OR^5$, $SR^5$, $CONR^5R^6$, $NHCOR^5$, $COOR^5$, $NR^5OR^6$, $NR^5R^6$, or $PR^5R^6$;
X/Y can be —O—, —S—, —P($R^5$)—, or N($R^5$)—;
each of $R^1$ through $R^4$, and $R^{7n}$ and $R^{8n}$, includes H, I, F, Cl, Br, CHO, OH, $NH_2$, $NO_2$, $OR^5$, $SR^5$, $CONR^5R^6$, $NHCOR^5$, $COOR^5$, $NR^5OR^6$, $NR^5R^6$, $PR^5R^6$, or from alkyl, alkoxyl, aralkyl, aryl or cycloalkyl groups having 1 to 9 carbon atoms;
each of R5 and R6 includes H, alkyl, alkoxyl, aralkyl, aryl or cycloalkyl groups having 1 to 9 carbon atoms; and
$R^1/R^2$, $R^1/R^3$, $R^3/R^4$, $R^1/R^{7n}$, or $R^{7n}/R^{8n}$ can be —O—, —S—, —P($R^5$)—, N($R^5$)—, or a cycloalkyl group having 1 to 9 carbon atoms.

In some embodiments, 3-fluoropropane-1,2-diol (FOH) ($R^1=R^2=R^3=R^5=H$, n=2, m=0 in formula I) is exemplified as an active agent of the compositions disclosed herein. FOH has two enantiomeric isomers (2r)-3-fluoropropane-1, 2-diol (rFOH) and (2s)-3-fluoropropane-1,2-diol (sFOH). FOH is a nonvolatile chemical having a boiling point of 205.4° C. at 760 mm Hg, a flash point of 87.2° C., and a density of 1.192 g/cm³. FOH is stable under normal temperature and pressure. The chemical synthesis of FOH is known in the art (Dummel et al., *J. Med. Chem.* 12(2): 347 (1969)). The chemical structure of FOH, representing both rFOH and sFOH, is shown below:

F—CH₂—CH(OH)—CH₂—OH

One of ordinary skill in the art would understand that enantiomeric isomers of the compounds disclosed herein are also encompassed in this disclosure. For example, although R-form of FOH may be more active than S-form of FOH, both enantiomers exhibit good pesticidal activities. In some embodiments, a racemic mixture, e.g., a 1:1, 1:2, 1:3, 1:4, 1:5, 1:6, 1:7, 1:8, 1:9, 1:10, 1:15, 1:20, 1:25, 1:30, 1:35, 1:40, 1:45, 1:50, 1:55, 1:60. 1:65, 1:70, 1:75, 1:80, 1:85, 1:90, 1:95, 1:99, 99:1, 95:1, 90:1, 85:1, 80:1, 75:1, 70:1, 65:1, 60:1, 55:1, 50:1, 45:1. 40:1, 35:1, 30:1, 25:1, 20:1, 15:1, 10:1, 9:1, 8:1, 7:1, 6:1, 5:1, 4:1, 3:1, or 2:1 mixture of R-form and S-form, can be used. In some embodiments, a racemic mixture of either form may range from 0.1% to 100%.

III. Nucleobase and Nucleoside Derivatives as the Active Agents

The compositions disclosed herein can contain nucleobases and nucleosides represented by either molecular formula III or formula IV:

Formula III

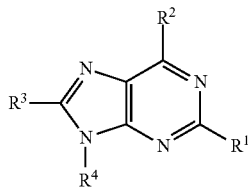
Formula IV wherein:

each of $R^1$, $R^2$ and $R^3$ includes H, F, $OR^5$, I, Cl, Br, CHO, $SR^5$, $CONHR^5$, $CON(R^5)_2$, $COOR^5$, an alkyl, an alkoxyl, an aralkyl, or an aryl group having 1 to 9 carbon atoms;

$R^4$ includes fluorinated or non-fluorinated carbohydrates, or polyhydroxy compounds having 1 to 9 carbon atoms; and $R^5$ includes H, an alkyl, an aralkyl, or an aryl group having 1 to 9 carbon atoms.

IV. Compositions Comprising Active Agents and Inactive Ingredients

In one aspect, the chemical compounds and derivatives encompassed in this patent document may be formulated to produce pesticides containing one or more attractant(s) that have low risks of poisoning humans and animals, and can be well managed to avoid environment pollution since serious toxicity exhibits only after ingestion. If not ingested, no death was found when pests were exposed to the active ingredients, such as rFOH, at a concentration 100-fold as high as the LD50. The disclosed active agents exhibit toxic effects upon ingestion by pests and become substrates in bioenergetic systems, thereby destroying enzymatic activity in metabolic pathways and cellular process. While conjugation of the enzymes with the substrates destroys enzyme functions, the process detoxifies the substrates. In some embodiments, the active agents disclosed in this patent document are nonvolatile and/or nontoxic upon direct skin or mucosal contact. In some embodiments, the active agents or derivatives, in combination with inactive ingredient(s), form gustatory attractants. With or without olfactory attractants such as odorants as an inactive ingredient, the pesticides promote active ingestion of the compounds by the pests, thereby further reducing the concentration required for killing pests. Accordingly, the pesticides disclosed in this patent document have lower toxicity to humans and animals, and to environment comparing to conventional pesticides.

In some embodiments, the amount of the one or more active agents (e.g., a polyalcohol, carbohydrate, nucleobase or nucleoside) is from 0.001% to 1%, from 0.1% to 25%, from 0.5% to 20%, from 1% to 15%, from 3% to 10%, or from 5% to 8% of the total weight of the composition. In some embodiments, the amount of the active agent is about 0.1%, about 0.5%, about 1%, about 2%, about 3%, about 5%, about 8%, about 10%, about 15%, about 20% or about 25% of the total weight of the composition. One of ordinary skill in the art can optimize the concentration of the one or more active agents to achieve the desired pest control effect.

In addition to the active agent(s), the compositions disclosed herein further contain one or more inactive ingredients which function as attractants to induce active ingestion of the compositions by the pests. The combination of the active agents, e.g., one or more chemical compounds represented by formulas I to IV, and one or more inactive ingredients achieves a synergistic effects in pest control. Due to the synergistic effect, a significantly less amount of the active agent(s) can be used in the composition to achieve the same pest control effect, thereby improving the safety of the pesticides to human and environment, and reducing the pressure in generating pesticide resistant mutant strains.

In certain embodiments, the active agent is or includes 3-fluoropropane-1,2-diol, including its stereoisomers such as enantiomers ((2R)-3-fluoropropane-1,2-diol and (2S)-3-fluoropropane-1,2-diol) and racemic mixtures.

In certain embodiments, the attractant includes a food attractant, e.g., a sugar such as sucrose, dextrose, fructose, and lactose, and other saccharides and polyols. In some embodiments, a combination of four or more attractants including sucrose, dextrose, sodium citrate, citric acid, sodium monobasic phosphate, or adenine is used. In other embodiments, the attractant includes a sex attractant, or an olfactory attractant. The attractant can be a synthetic product or a natural product such as honey and syrup. The attractant can be in any amount (w/w %) in the composition such that the composition induces active ingestion by the pests. For example, the attractant(s) can be in an amount from 0.001% to 1%, from 1% to 50%, from 5% to 45%, from 10% to 30%, or from 15% to 25% of the total weight of the composition. In some embodiments, the attractant(s) is in an amount about 1%, about 5%, about 10%, about 15%, about 20%, about 25%, about 30%, about 35%, about 40%, about 45%, or about 50% of the total weight of the composition.

It is within the purview of one of ordinary skill in the art to optimize the type and/or the amount of the attractant depending on the particular species, sex, body weight, and the metabolic rate of the pest. For example, an attractant comprising a sugar and apple cider vinegar can improve the killing rate of FOH for flies. Likewise, a formula comprising a sugar and sesame oil can improve the killing rate of FOH for cockroaches.

In some embodiments, the attractant further comprises a nutrimental solution, such as a citrate-phosphate-dextrose plus adenine (CPDA) solution (for mosquitoes bedbugs, fleas, ticks and others); Ringer's Lactate solution (which is physiological saline plus L (+)-lactic acid at concentrations ranging from 0.1% to 85%) (for mosquitoes); apple cider vinegar (for flies); a combination of 0.03% phosphoric acid, 0.4% propionic acid, sugar and dried powdered yeast (for flies); a combination of 10% sugar, 1% sesame oil or other eatable oils (for cockroaches); a combination of 350 g rolled oats, 350 g wheat feed, 50 g linseed cake, 120 g grass meal, 35 g casein, 25 g dried powdered yeast, 25 g sucrose, 50 ml linseed oil, 50 ml arachis oil and 1 l g table salt mixture (for cockroaches and rodents); a combination of sugar, sodium chloride, disodium phosphate, yeast extract, bacto-trypton, enzymatic digest of animal tissue and/or dried blood powder (for various bacteria and fungi); and a Mueller Hinton broth (for various bacteria and fungi). In some embodiments, an exemplary pesticide composition comprising FOH in Brain Heart Infusion medium can kill various bacteria and fungi. In some embodiments, the nutrimental solution comprises sugar, honey or syrup.

In some embodiments, the attractant includes an environmental attractant created by a device or devices to provide a desirable pH value, light, sound, vibration, wind, heat, humidity, gas (such as $CO_2$), or a combination thereof to attract a particular species of pests. For example, mosquitoes are attracted by an elevated temperature in a range from about 25° C. to about 46° C., preferably about 37° C.

The composition comprising one or more active agents and one or more attractants disclosed in this patent document kills at least 10%, at least 20%, at least 30%, at least 40%, at least 50%, at least 60%, at least 70%, at least 80%, at least 90%, or about 100% of the population of the pests upon ingestion of the composition. In some embodiments, the composition disclosed in this patent document has a killing rate which is at least 5%, at least 10%, at least 20%, at least 30%, at least 40%, at least 50%, at least 60%, at least 70%, at least 80%, at least 90%, at least 100%, at least 1.5-fold, at least 2-fold, at least 3-fold, at least 4-fold, at least 5-fold, at least 6-fold, at least 7-fold, at least 8-fold, at least 9-fold, or at least 10-fold higher than the killing rate of a composition containing the same active agent without any attractant.

In another aspect, this patent document discloses a method of pest control. The method includes a step of exposing a pest to the composition disclosed above. In some embodiments, a feeding device or a feeder containing one or more active agents and one or more inactive ingredients can be used. The device or the feeder can take any size or shape, e.g., a small-neck bottle. An exemplary moisture mosquito feeder contains a cotton rod extended out of a small-neck bottle and absorbed with the pesticides in the bottle. Moreover, the feeder may or may not be placed in a temperature controlled device ranging from about 25° C. to about 46° C., or from about 33° C. to about 39° C.

In yet another aspect, this patent document provides a method of preventing pest-borne, infectious diseases. The method includes a step of exposing a pest to the composition disclosed above. In some embodiments, the method includes applying an ointment comprising the composition disclosed above. The ointment can further comprise a natural product such as honey or syrup. The method is particularly useful for preventing diseases caused by antibiotic-resistant bacteria or fungi.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Only a few implementations and examples are described and other implementations, enhancements and variations can be made based on what is described and illustrated in this patent document.

Example 1 Toxicity of rFOH by Air Exposure

Base attractant to mosquitoes: the base inactive ingredients contained 10% sucrose in CPDA solution. The CPDA contained 3.33 g sodium citrate, 0.376 g citric acid, 4.02 g glucose, 0.28 g sodium monobasic phosphate, and 0.346 g adenine in 1 liter of solution. (2R)-3-fluoropropane-1,2-diol (rFOH) was used as the active agent at a concentration of 1%.

100 mosquitoes were placed in a 6-liter cage with a container containing 1% rFOH in 10% sucrose with CPDA for 48 hours at room temperature (25-28° C.). The container was protected with a net to prevent ingestion of rFOH by the mosquitoes. No death of mosquito was observed after 48 hours of exposure, indicating that rFOH is nontoxic or low toxic if not ingested. The same result was obtained even when 10% of rFOH was used.

Example 2 Efficacy of rFOH by Ingestion

Female mosquitoes were used in the experiment because only female mosquitoes bite humans and animals and transmit infectious diseases.

The same base of inactive ingredients as described above was used in this experiment. (2R)-3-fluoropropane-1,2-diol (rFOH) was used as the active agent at various concentrations. A sugar feeder containing 10% sucrose, which is a regular mosquito feeder in a laboratory setting, was used as a regular food source in free choice studies. A free choice study allows the pests to select which feeder to feed on when given two or more choices.

In a two-choice test, a 6-liter cage was supplied with two feeders, one contained 5% rFOH and 10% sucrose in CPDA and the other one contained 10% sucrose without any rFOH or CPDA. 100 female mosquitoes were placed in the cage having the two feeders such that the mosquitoes chose freely which feeder to feed on. After 24 hours of feeding in the cage, over 80% of mosquitoes were dead. In contrast, no death was observed in the control cage, supplied with 10% sucrose only, in a parallel study. When the concentration of rFOH was reduced to 1% or 0.15%, its effectiveness remained the same. Over 80% of mosquitoes were dead due to 24 hours of feeding with rFOH.

Subsequent to 24 hours of feeding, rFOH feeder was removed from the cage and a regular sugar feeder (10% sucrose) was provided. In the next day, 5-20% of residual death was observed, indicating a delayed death after rFOH ingestion. Accordingly, the active agent exhibited toxicity when metabolized in the body of the pest. In the parallel control groups, feeding on 10% sucrose without any rFOH, less than 5% of death, often 0%, was observed for the same period of time.

In a further study, mosquitoes were fasted for 24 hours before feeding to ensure that all mosquitoes have the capacity for food intake. A control experiment demonstrated that only less than 1% of death (0 or 1 mosquito death in each control group) was observed in mosquitoes fasted for 48 hours. Thus, fasting is not a cause of mosquito death during a series of experiments.

The experiments determined that 0.1% rFOH was sufficient to achieve 50% death (LD50) under various conditions. In one study, 100 mosquitoes were caged in a 6-liter space and fasted for 24 hours. Subsequently, the mosquitoes were fed on two feeders giving their free choices for 0.1% rFOH containing 10% sucrose in CPDA or 10% sucrose without rFOH for 24 hours, resulting in 43% death. In a parallel study in which the cage was supplied with a single feeder, the 0.1% rFOH feeder containing 10% sucrose in CPDA, which caused 44% of death after 24 hours of feeding. Similar death rate was observed in studies that mosquitoes were not fasted before treatment. The data showed that mosquitoes had even better preference for the rFOH feeder than sugar feeder when given the free choices between feeders. See Tables 2-4 below.

Once the rFOH feeder was removed and replaced by a sugar feeder, a residual death was observed within the next 24 hours such that the total death rate was 46-64% at 0.1% rFOH. A concentration of 0.15% or more of rFOH was sufficient to achieve higher death rates.

In one study group, when the female mosquitoes were fed on a formula containing 0.1% rFOH in CPDA solution without any sucrose for 24 hours, the death rate decreased from over 55% to 10-25% in free choice studies. The death rate was further reduced to less than 10% when the female mosquitoes were fed on 0.1% rFOH in water without any sugar or CPDA. Thus, the presence of the inactive ingredients in the composition in combination with the active agent achieved a significantly improved killing effect.

The concentration of rFOH in the formulation was further optimized. Further studies demonstrated that 0.15% rFOH (corresponding to as few as 0.001 mg rFOH per mosquito, assuming a female mosquito could ingest as much as 0.6 µl of the composition) caused more than 90% death of female mosquitoes after 24 hours of feeding. For female mosquitoes, ingestion of 0.15% rFOH caused death within 2-5 hours.

Example 3 Various Concentrations of rFOH Achieved Similar Killing Rate

Similar experiments as disclosed above were performed with various rFOH concentrations under various conditions. The rFOH composition contained 10% sugar in CPDA solution unless specified otherwise. The results are summarized in the table below.

TABLE 1

| rFOH Conc. (%) | Treatment Period (hrs) | Fasting Condition | Treatment Condition | Death Rate |
|---|---|---|---|---|
| 5% | 24 | Not fasted | Sugar feeder provided for free choice | >85% |
| 5% | 24 | Not fasted | Sugar feeder not provided | 94% |
| 1% | 24 | Not fasted | Sugar feeder not provided | 93% |

The data demonstrate that 1% rFOH was sufficient to achieve a maximal killing rate, which is over 90%.

Example 4 Female Mosquitoes Required Higher Concentration of rFOH than Male Mosquitoes Similar experiments as disclosed above were performed on female mosquitoes and male mosquitoes. The rFOH composition contained 10% sugar in CPDA solution unless specified otherwise. The results are summarized in the table below.

TABLE 2

| Sex | rFOH Conc. (%) | Treatment Period (hrs) | Fasting Condition | Treatment Condition | Death Rate |
|---|---|---|---|---|---|
| Male | 0.1% | 24 | 24 hrs fasting | Sugar feeder provided for free choice | 95% |
| Female | 0.1% | 24 | 24 hrs fasting | Sugar feeder provided for free choice | 46-64% |
| Female | 0.15% | 24 | 24 hrs fasting | Sugar feeder provided for free choice | 55-80% |
| Female | 0.15% | 24 | 24 hrs fasting | Sugar feeder not provided | 95-98% |

The data demonstrate that a higher concentration of rFOH is required for female mosquitoes than for male mosquitoes to achieve about the same killing rate due to larger sizes of the female. Thus, the concentration of FOH can be adjusted depending on the average body weight of the targeting pest to optimize the pest control effect.

Example 5 Determination of LD50 for Female Mosquitoes

Similar experiments as disclosed above were performed on female mosquitoes to determine LD50. The rFOH composition contained 10% sugar in CPDA solution unless specified otherwise. The results are summarized in the table below.

TABLE 3

| rFOH Conc. (%) | Treatment Period (hrs) | Fasting Condition | Treatment Condition | Death Rate |
|---|---|---|---|---|
| 0.1% | 24 | Not fasted | Sugar feeder provided for free choice | 64% |
| 0.1% | 24 | 24 hrs fasting | Sugar feeder provided for free choice | 46-64% |
| 0.1% | 24 | 24 hrs fasting | Sugar feeder not provided | 65% |

The data demonstrate that the LD50 of rFOH for female mosquitoes was about 0.1%.

Example 6 Effects of Inactive Ingredients

Similar experiments as disclosed above were performed on female mosquitoes with 0.1% rFOH and various inactive ingredients. The results are summarized in the table below.

TABLE 4

| Sugar Conc. (%) | CPDA | Others | rFOH Conc. (%) | Treatment Period (hrs) | Fasting Condition | Treatment Condition | Death Rate |
|---|---|---|---|---|---|---|---|
| 0% | No | No | 0.1% | 24 | 24 hrs fasting | Sugar feeder provided for free choice | 4-8% |
| 0% | Yes | No | 0.1% | 24 | 24 hrs fasting | Sugar feeder provided for free choice | 13-17% |
| 10% | No | No | 0.1% | 24 | 24 hrs fasting | Sugar feeder provided for free choice | 44-50% |
| 10% | Yes | No | 0.1% | 24 | 24 hrs fasting | Sugar feeder provided for free choice | 46-64% |
| 10% | Yes | No | 0.1% | 24 | 24 hrs fasting | Sugar plus CPDA feeder provided for free choice | 59-80% |

TABLE 4-continued

| Sugar Conc. (%) | CPDA | Others | rFOH Conc. (%) | Treatment Period (hrs) | Fasting Condition | Treatment Condition | Death Rate |
|---|---|---|---|---|---|---|---|
| 5% | Yes | 50% corn syrup | 0.1% | 24 | 24 hrs fasting | Sugar feeder provided for free choice | 22-30% |
| 5% | Yes | 25% Maple Syrup | 0.1% | 24 | 24 hrs fasting | Sugar feeder provided for free choice | 26-47% |
| 5% | Yes | 5% maltose | 0.1% | 24 | 24 hrs fasting | Sugar feeder provided for free choice | 54% |

The data demonstrate that rFOH alone without any inactive ingredient such as sugar or CPDA resulted in minimal death rate when a 10% sugar feeder was provided for free choice. rFOH in CPDA without any sugar was less effective than rFOH in sugar and CPDA. rFOH in sugar alone was about as effective as rFOH in sugar and CPDA. Finally, when a sugar plus CPDA feeder was given as a free choice, the killing rate was improved comparing to when a sugar only feeder as a free choice (See rows 4 and 5 in Table 4).

Example 7 Effects of Other Active Agents

Similar experiments as disclosed above were performed on female mosquitoes using different active agents at various concentrations. The active agent composition contained 10% sugar in CPDA solution unless specified otherwise. The results are summarized in the table below.

TABLE 5

| Active Agent and Conc. (%) | Chemical Formula | Treatment Period (hrs) | Fasting Condition | Treatment Condition | Death Rate |
|---|---|---|---|---|---|
| sFOH at 0.5% | Formula I (n = 2, m = 0, $R^1$=$R^2$=$R^3$=$R^5$=H) | 24 | 24 hrs fasting | Sugar feeder not provided | >85% death was found for a week after treatment was removed |
| sFOH at 0.3% | Formula I (n = 2, m = 0, $R^1$=$R^2$=$R^3$=$R^5$=H) | 24 | 24 hrs fasting | Sugar feeder not provided | 42-68% death was found for a week after treatment was removed |
| 2-Amino-1,3-propanediol (CAS 534-03-2) at 0.5% | Formula II (m = 1, X=Y=OH, $R^1$=$R^2$=$R^3$=$R^4$=H, $R^{71}$=$NH_2$, $R^{81}$=H) | 24 | 24 hrs fasting | Sugar feeder not provided | 16% |
| 1,1-Bis(hydroxymethyl)cyclobutane (CAS 4415-73-0) at 0.5% | Formula II (m = 1, X=Y=OH, $R^1$=$R^2$=$R^3$=$R^4$=H, $R^{71}$/$R^{81}$=$CH_2CH_2$) | 24 | 24 hrs fasting | Sugar feeder not provided | 50% |
| 3-Bromopropane-1,2-diol (CAS 4704-77-2) at 0.15% | Formula II (m = 1, X=Br, Y=OH, $R^1$=$R^2$=$R^3$=$R^4$=H, $R^{71}$=OH, $R^{81}$=H) | 24 | 24 hrs fasting | Sugar feeder provided for free choice | 30-52% death was found for a week after treatment was removed |
| 3-Bromopropane-1,2-diol (CAS 4704-77-2) at 0.2% | Formula II (m = 1, X=Br, Y=OH, $R^1$=$R^2$=$R^3$=$R^4$=H, $R^{71}$=OH, $R^{81}$=H) | 24 | 24 hrs fasting | Sugar feeder not provided | >85% death was found for a week after treatment was removed |
| 3-Chloro-1,2-propanediol (CAS 96-24-2) at 0.15% | Formula II (m = 1, X=Cl, Y=OH, $R^1$=$R^2$=$R^3$=$R^4$=H, $R^{71}$=OH, $R^{81}$=H) | 24 | 24 hrs fasting | Sugar feeder not provided | >85% |
| 1,2-cyclohexanediol (CAS 931-17-9) at 0.5% | Formula II (m = 2, X=Y=$R^2$=$R^3$=$R^{81}$=$R^{82}$=H, $R^1$/$R^4$=$CH_2CH_2CH_2CH_2$, $R^{71}$=$R^{72}$=OH) | 24 | 24 hrs fasting | Sugar feeder not provided | 22% |
| 2'-Deoxy-5-fluorouridine (CAS 50-91-9) | Formula III ($R^1$=OH, $R^2$=F, $R^3$=H, | 24 | 24 hrs fasting | Sugar feeder not provided | 24% |

TABLE 5-continued

| Active Agent and Conc. (%) | Chemical Formula | Treatment Period (hrs) | Fasting Condition | Treatment Condition | Death Rate |
|---|---|---|---|---|---|
| at 2% | $R^4$ = 2-deoxyribose group) | | | | |
| 4-Deoxy-4-fluoro-β-D-glucopyranose (CAS 27108-04-9) at 1% | Formula I ($R^1$=$R^2$=$R^3$=$R^4$=H, n = m = 2, $R^5$=CHO) | 2 | 18 hrs fasting | Membrane feeding due to small amount of the compound. Feeding lasted for 1 hour and 45 minutes before a sugar feeder was provided. | 2% in the first hour, 10% in 2 hours, 17% in 24 hours |
| 2,2-Dimethyl-1,3-propanediol (CAS 126-30-7) at 0.5% | Formula II (m = 1, X=Y=OH, $R^1$=$R^2$=$R^3$=$R^4$=H, $R^{71}$=$R^{81}$=Me) | 24 | 24 hrs fasting | Sugar feeder provided for free choice | 10% |
| 2,3-Dimethylbutane-2,3-diol (CAS 76-09-5) at 1.5% | Formula II (m = 0, X=Y=OH, $R^1$=$R^2$=$R^3$=$R^4$=Me) | 24 | 24 hrs fasting | Sugar feeder not provided | 53% |
| 2-Fluoroadenine (CAS 700-49-2) at 0.2% | Formula III ($R^1$=F, $R^2$=$NH_2$, $R^3$=$R^4$=H) | 24 | 24 hrs fasting | Sugar feeder provided for free choice | 30% |
| 2-Fluoroadenosine (CAS 146-78-1) at 1% | Formula IV ($R^1$=F, $R^2$=$NH_2$, $R^3$=$R^4$=H) | 24 | 24 hrs fasting | Sugar feeder not provided | 22% within 24 hrs after treatment removed, 47% within 2 days after treatment removed, 64% within 3 days after treatment removed, and 75-80% within 4 days after treatment removed |
| Gemcitabine (CAS 95058-81-4) at 0.5% | Formula III ($R^1$=$NH_2$, $R^2$=$R^3$=H, $R^4$ = 2-deoxy-2,2-difluororibose group) | 24 | Not fasted | Sugar feeder provided for free choice | 3% within 24 hrs after treatment removed, 36% within 2 days after treatment removed, and 63%-66% within 3 days after treatment removed |
| 2-Methyl-1,3-propanediol (CAS 2163-42-0) at 0.5% | Formula II (m = 1, X=Y=OH, $R^1$=$R^2$=$R^3$=$R^4$=H, $R^{71}$=Me, $R^{81}$=H) | 24 | 24 hrs fasting | Sugar feeder not provided | 12% |
| 2-Penyl-1,3-propanediol (CAS 1570-95-2) at 1.5% | Formula II (m = 1, X=Y=OH, $R^1$=$R^2$=$R^3$=$R^4$=H, $R^{71}$=Ph, $R^{81}$=H) | 24 | 24 hrs fasting | Sugar feeder not provided | 61% |
| (R)-(+)-2-Chloropropionic acid (CAS 7474-05-7) at 0.5% | Formula II (m = 0, X=COOH, Y=H, $R^1$=$R^3$=$R^4$=H, $R^2$=Cl) | 24 | 24 hrs fasting | Sugar feeder not provided | 10% |

The results for 4-deoxy-4-fluoro-β-D-glucopyranose (CAS 27108-04-9) was not comparable to the killing rates achieved by other active agents due to the use of membrane feeding method. This is because membrane feeding provides only a small space accessible to a limited number of mosquitoes for feeding.

The death caused by FOH and 4-deoxy-4-fluoro-3-D-glucopyranose was sooner than death caused by some other active agents. With respect to gemcitabine (CAS 95058-81-4), the death rates in day two and day three after the treatment was removed were increased significantly and finally reached 66%. Similarly, 2-fluoroadenosine (CAS 146-78-1) caused a "delayed" death, and the death rate reached 75-80% in four days after treatment was removed. "Delayed" death was also occurred when sFOH and 3-bromopropane-1,2-diol (BrOH, CAS 4704-77-2) used as the active agents. The "delayed" death may be caused by different breakdown mechanism of various active agents upon ingestion.

Example 8 Effects of Olfactory Attractants

It is well known that olfaction guides animal behavior. Olfactory attractants can lure remote mosquitoes to approach the pesticides and stimulate mosquito appetites. Using experimental setting disclosed above, it was found, with addition of olfactory attractants, 20% to 40% more mosquitoes were killed in studies when mosquitoes were given free choices between the sugar feeder and rFOH containing 10% sugar and CPDA plus olfactory attractants compared to the same experiments without addition of the olfactory attractants.

Example 9 Effects of Environmental Attractants

Environmental attractants such as heat can be used in combination with the compositions disclosed in this patent document. The effects of CPDA were tested at different temperatures. At room temperature, CPDA attracted 0 to 3 mosquitoes; whereas at 37° C., the same amount of CPDA attracted 8 to 65 mosquitoes.

In a similar study, CPDA placed at 37° C. attracted 58 to 125 times more mosquitoes than CPDA placed at room temperature.

Example 10. Effects on Bacteria

The effects of pesticides disclosed herein on various bacteria were tested by determining the minimal inhibitory concentration (MIC) of the pesticides. MIC of an antimicrobial agent is the lowest concentration of the antimicrobial agent that inhibits a given bacterial isolate from multiplying and producing visible growth in the test system. The MIC of rFOH and BrOH was determined in the laboratory by incubating a known quantity of bacteria with a series of dilutions of the active agents and comparing their effects with those of known antimicrobial agents. Table 6 lists the representative bacterial strains and the conditions in MIC tests. Antimicrobial tests of the active agents were conducted according to "Methods for Dilution Antimicrobial Susceptibility Tests for Bacteria That Grow Aerobically" by Clinical and Laboratory Standards Institute (CLSI) (CLSI document M07-A9, 2012). In the study, methicillin/oxacillin resistant *Staphylococcus aureus* (MRSA) strain (ATCC 43300) was routinely under screening with 4 ug/ml oxacillin. *Escherishia coli* DH5α was a nonpathogenic laboratory strain. When DH5α were transformed with a pcDNA3 plasmid, the DH5α showed robust resistance to antibiotic agents ampicillin and neomycin. When the DH5α/plasmid (DH5P) colony was used, the colony was maintained in the presence of 100 ug/ml ampicillin.

TABLE 6

Bacterial Strains and Study Conditions

| Organism | Methicillin/oxacillin resistant *Staphylococcus aureus* (MRSA) | *Escherishia coli* DH5α |
| --- | --- | --- |
| Gram Type | positive | negative |
| Medium | Mueller Hinton broth/agar with 2% NaCl and 50 ug/ml $CaCl_2$ | Tryptic soy broth/agar |
| Incubation temperature and time | 35° C. for 24 hrs | 37° C. for 24 hrs |
| Antibiotic reagents for screening and MIC | 4 ug/ml oxacillin for MRSA screening and cefoxitin for MIC testing | ampicillin |

MIC tests were conducted in 96 well microtiter plates with a total volume of 150 ul broth in each well. The directly colony suspension method (CLSI document M07-A9, 2012) was applied to obtain MIC for antimicrobial tests of the active agents. After colonies were freshly incubated overnight, colonies were suspended in sterile water to adjust the inoculum to a turbidity equivalent to a 0.5 McFarland standard (corresponding to approximately $1.5 \times 10^8$ CFU/ml). Within 10 minutes, the inoculum was adjusted by dilution in broth to reach a final concentration of $5 \times 10^5$ CFU/ml. A series of various concentrations of the active agents were applied to determine the MIC. In the same microtiter plate, an internal standard formulated by a concentration series of standard antibiotic agent was incubated in parallels to allow for back-to-back comparison. Within a 96 microtiter plate, a few wells did not add bacteria as the negative control.

The MIC results for rFOH and BrOH are shown in Table 7. At a concentration of 0.4%, rFOH was able to completely inhibit normal and antibiotic resistant strains. At this concentration, it was as effective as 48 ug/ml of cefoxitin when it was used against Methicillin/oxacillin resistant *Staphylococcus aureus* (MRSA), as effective as 19 ug/ml ampicillin when used against gram-negative strain *Escherishia coli* DH5α, and as effective as 240 ug/ml ampicillin when used against DH5P (Table 7). Interestingly, although similar in chemical structures, BrOH was much more effective against *E. coli* with an MIC of 0.025%. Its MICs against DH5P and MRSA were 0.2% and 2.5%, respectively.

TABLE 7

MIC of Active Agents against Various Bacterial Strains

| Organism | MIC rFOH | MIC BrOH | Comparable Effectiveness |
| --- | --- | --- | --- |
| Methicillin/oxacillin resistant Staphylococcus aureus (MRSA) | 0.40% | 2.5% | 48 ug/ml cefoxitin |
| Escherishia coli DH5α | 0.43% | 0.025% | 19 ug/ml |
| Escherishia coli DH5α transformed with a pcDNA3 plasmid that contained neomycin and ampicillin resistant genes (DH5P) | 0.40% | 0.20% | 240 ug/ml |

While this document contains various specifics, these should not be construed as limitations on the scope of an invention or of what may be claimed, but rather as descriptions of features specific to particular embodiments of the invention. Variations and enhancements of the described embodiments and other embodiments can be made based on what is described.

We claim:

1. A method of mosquito control comprising feeding a population of mosquitos with a composition comprising one or more active agents, and one or more attractants or nutrients, wherein the active agent includes 3-fluoropropane-1,2-diol, 2-amino-1,3-propanediol, 1,1-bis(hydroxymethyl)cyclobutene, 3-bromopropane-1,2-diol, 3-chloro-1,2-propanediol, 1,2-cyclohexanediol, 2'-deoxy-5-fluorouridine, 4-deoxy-4-fluoro-β-D-glucopyranose, 2,2-dimethyl-1,3-propanediol, 2,3-dimethylbutane-2,3-diol, 2-fluoroadenine, 2-fluoroadenosine, gemcitabine, 2-methyl-1,3-propanediol, 2-penyl-1,3-propanediol, or 2-chloropropionic acid, and wherein the one or more attractants include a food attractant, a sex attractant, an olfactory attractant, or an environmental attractant.

2. The method of claim 1, wherein the concentration of the one or more active agents is from 0.001% to 1%, from 0.1% to 25%, from 0.5% to 20%, from 1% to 15%, from 3% to 10%, or from 5% to 8% of the total weight of the composition.

3. The method of claim 1, wherein the composition comprises a combination of four or more attractants that include sucrose, dextrose, sodium citrate, citric acid, sodium monobasic phosphate, or adenine.

4. The method of claim 1, wherein the environmental attractant includes pH, light, sound, vibration, wind, heat, humidity, or gas.

5. The method of claim 1, wherein the concentration of the one or more attractants is from 0.001% to 1%, from 1% to 50%, from 5% to 45%, from 10% to 30%, or from 15% to 25% of the total weight of the composition.

6. The method of claim 1, wherein the composition kills at least 10%, at least 20%, at least 30%, at least 40%, at least 50%, at least 60%, at least 70%, at least 80%, at least 90%, or about 100% of the population of the mosquitos upon ingestion of the composition.

* * * * *